(12) United States Patent
Prasad et al.

(10) Patent No.: US 7,756,237 B2
(45) Date of Patent: Jul. 13, 2010

(54) ABSOLUTE NUCLEAR MATERIAL ASSAY

(75) Inventors: Manoj K. Prasad, Pleasanton, CA (US);
Neal J. Snyderman, Berkeley, CA (US);
Mark S. Rowland, Alamo, CA (US)

(73) Assignee: Lawrence Livermore National Security, LLC, Livermore, CA (US)

( * ) Notice: Subject to any disclaimer, the term of this patent is extended or adjusted under 35 U.S.C. 154(b) by 0 days.

(21) Appl. No.: 11/244,088

(22) Filed: Oct. 4, 2005

(65) Prior Publication Data

US 2006/0081787 A1     Apr. 20, 2006

Related U.S. Application Data

(60) Provisional application No. 60/620,304, filed on Oct. 19, 2004.

(51) Int. Cl.
*G21G 1/06* (2006.01)
(52) U.S. Cl. ........................ 376/159; 376/257; 376/158; 376/156
(58) Field of Classification Search ................. 376/159, 376/257, 158, 156
See application file for complete search history.

(56) References Cited

U.S. PATENT DOCUMENTS

| | | | |
|---|---|---|---|
| 3,456,113 A | | 7/1969 | Keepin |
| 4,201,912 A | | 5/1980 | Evans et al. |
| 4,483,816 A | | 11/1984 | Caldwell et al. |
| 4,617,466 A | | 10/1986 | Menlove et al. |
| 4,920,271 A | * | 4/1990 | Arnone ................... 250/390.01 |
| 5,197,130 A | * | 3/1993 | Chen et al. ...................... 712/3 |
| 6,341,150 B1 | * | 1/2002 | Ivanov et al. ................ 376/159 |
| 6,420,712 B1 | * | 7/2002 | Menlove et al. ......... 250/390.01 |
| 6,509,563 B1 | * | 1/2003 | McElroy et al. ............. 250/291 |
| 2002/0125439 A1 | * | 9/2002 | Caldwell et al. ............ 250/395 |
| 2005/0105665 A1 | | 5/2005 | Grodzins et al. |

FOREIGN PATENT DOCUMENTS

JP          06300887 A         10/1994

OTHER PUBLICATIONS

UCRL-TR-206043: Frank et al., "Application of Neutron Correlation Techniques to Warhead Authentication: Feasibility and Conceptual Requirements—Monte Carlo Simulations and Statistical Analysis," Aug. 13, 2004.*
Ensslin et al., "Application Guide to Neutron Multiplicity Counting," LA-13422M, Nov. 1998.*
ESARDA, NCC, "Passive Neutron Coincidence Counting TEachniques for PU Mass Determination," Mar. 1, 2004.*

(Continued)

*Primary Examiner*—Rick Palabrica
(74) *Attorney, Agent, or Firm*—Eddie E. Scott; John H. Lee

(57) ABSTRACT

A method of absolute nuclear material assay of an unknown source comprising counting neutrons from the unknown source and providing an absolute nuclear material assay utilizing a model to optimally compare to the measured count distributions. In one embodiment, the step of providing an absolute nuclear material assay comprises utilizing a random sampling of analytically computed fission chain distributions to generate a continuous time-evolving sequence of event-counts by spreading the fission chain distribution in time.

4 Claims, 2 Drawing Sheets

OTHER PUBLICATIONS

Hicks, et al., "probabilities of Prompt-Neutron Emission from Spontaneous Fission," Phys. Rev., vol. 101, No. 3, Feb. 1, 1956, pp. 1016-1020.*

Ensslin, N., et al., "Application Guide to Neutron Multiplicity Counting," LA-13422-M, UC-700, Los Alamos National Laboratory, Nov. 1998.

Hage, W., et al., "Correlation Analysis with Neutron Count Distributions in Randomly or Signal Triggered Time Intervals for Assay of Special Fissile Materials," Nuclear Science and Engineering, 89, pp. 159-176, (1985).

Furuhashi, A., et al, "Third Moment of the Number of Neutrons Detected in Short Time Intervals," Journal of Nuclear Science and Technology, 5 (2), pp. 48-59, (Feb. 1968).

Prasad, M.K., et al., "Statistical Theory of Fission Chains and Generalized Poisson Neutron Counting Distributions," University of California, Lawrence Livermore National Laboratory, pp. 1-41 Apr. 16, 2002.

Prasad, M.K., et al., "Statistical Theory of Fission Chains and Generalized Poisson Neutron Counting Distributions," University of California, Lawrence Livermore National Laboratory, pp. 1-38, Aug. 6, 1991.

* cited by examiner

ABSOLUTE NUCLEAR MATERIAL ASSAY

CROSS-REFERENCE TO RELATED APPLICATIONS

This application claims the benefit of U.S. Provisional Patent Application No. 60/620,304 filed by Manoj Prasad, Neal J. Snyderman, and Mark S. Rowland Oct. 19, 2004 and titled "Absolute Nuclear Material Assay." U.S. Provisional Patent Application No. 60/620,304 is incorporated herein by this reference.

The United States Government has rights in this invention pursuant to Contract No. W-7405-ENG-48 between the United States Department of Energy and the University of California for the operation of Lawrence Livermore National Laboratory.

BACKGROUND

1. Field of Endeavor

The present invention relates to nuclear material assay and more particularly to an absolute nuclear material assay.

2. State of Technology

United States Patent Application No. 2005/0105665 by Lee Grodzins and Peter Rothschild for a system of detection of neutrons and sources of radioactive material, published May 19, 2005, provides the following state of technology information: "There is a need to find sources of radiation and other nuclear material that are clandestinely transported across national boundaries. The sources of clandestine nuclear material may be in the form of "dirty bombs" (e.g., a conventional explosive combined with radioactive nuclides designed to spread radioactive contamination upon detonation), fissile material, and other neutron and radiation emitting sources that may present a hazard to the public. During recent years, the United States government has placed mobile vehicles at strategic areas with gamma ray detectors dedicated to the task of finding fissile material. Atomic explosives may be made from $^{235}$U, a rare, naturally occurring, isotope of uranium that lives almost $10^9$ years, or $^{239}$Pu, a reactor-made isotope that lives more than $10^4$ years. $^{235}$U decays with the emission of gamma ray photons (also referred to as 'gammas'), principally at 185.6 keV and 205. 3 keV. $^{239}$Pu emits a number of gamma rays when it decays, the principal ones being at 375 keV and 413.7 keV. These gamma rays are unique signatures for the respective isotopes. But fissile material invariably contains other radioactive isotopes besides those essential for nuclear explosives. For example, weapons grade uranium may contain as little as 20% $^{235}$U; the rest of the uranium consists of other isotopes. The other uranium and plutonium isotopes reveal their presence by gamma rays emitted by their daughters. For example, a daughter of $^{238}$U emits a high energy gamma ray at 1,001 keV; a daughter of $^{232}$U, an isotope present in fissile material made in the former USSR, emits a very penetrating gamma ray at 2,614 keV; and a daughter of $^{241}$Pu emits gamma rays of 662.4 keV and 722.5 keV."

U.S. Pat. No. 4,201,912 issued May 6, 1980 to Michael L. Evans et al and assigned to The United States of America as represented by the United States Department of Energy, provides the following state of technology information: "A device for detecting fissionable material such as uranium in low concentrations by interrogating with photoneutrons at energy levels below 500 keV, and typically about 26 keV. Induced fast neutrons having energies above 500 keV by the interrogated fissionable material are detected by a liquid scintillator or recoil proportional counter which is sensitive to the induced fast neutrons. Since the induced fast neutrons are proportional to the concentration of fissionable material, detection of induced fast neutrons indicates concentration of the fissionable material."

U.S. Pat. No. 4,617,466 issued Oct. 14, 1986 to Howard O. Menlove and James E. Stewart and assigned to The United States of America as represented by the United States Department of Energy, provides the following state of technology information: "Apparatus and method for the direct, nondestructive evaluation of the .sup.235 U nuclide content of samples containing UF.sub.6, UF.sub.4, or UO.sub.2 utilizing the passive neutron self-interrogation of the sample resulting from the intrinsic production of neutrons therein. The ratio of the emitted neutron coincidence count rate to the total emitted neutron count rate is determined and yields a measure of the bulk fissile mass. The accuracy of the method is 6.8% (1.sigma.) for cylinders containing UF.sub.6 with enrichments ranging from 6% to 98% with measurement times varying from 3-6 min. The samples contained from below 1 kg to greater than 16 kg. Since the subject invention relies on fast neutron self-interrogation, complete sampling of the UF.sub.6 takes place, reducing difficulties arising from inhomogeneity of the sample which adversely affects other assay procedures."

U.S. Pat. No. 3,456,113 issued Jul. 15, 1969 to G. Robert Keepin provides the following state of technology information: "An apparatus and method of detecting, identifying and quantitatively analyzing the individual isotopes in unknown mixtures of fissionable materials. A neutron source irradiates the unknown mixture and the kinetic behavior of the delayed neutron activity from the system is analyzed with a neutron detector and time analyzer. From the known delayed neutron response of the individual fission species it is possible to determine the composition of the unknown mixture. Analysis of the kinetic response may be accomplished by a simple on-line computer enabling direct readout of isotopic assay."

SUMMARY

Features and advantages of the present invention will become apparent from the following description. Applicants are providing this description, which includes drawings and examples of specific embodiments, to give a broad representation of the invention. Various changes and modifications within the spirit and scope of the invention will become apparent to those skilled in the art from this description and by practice of the invention. The scope of the invention is not intended to be limited to the particular forms disclosed and the invention covers all modifications, equivalents, and alternatives falling within the spirit and scope of the invention as defined by the claims.

The present invention provides a system of absolute nuclear material assay of an unknown source. The present invention provides a system that relates, in detail, a correlated or uncorrelated chain of neutrons with what appears in an instrument (i.e., relates physical parameter to a measured quantity). How the chain of neutrons is used was traditionally related in a process that connects count sums to physical parameters of interest, such as multiplication. The limitations of prior art start with and are rooted in approximations in the detailed description of the neutron chain. These approximations, in the details of exactly how a chain is described and evolves in time, conspire to make the process of relating chains to physical parameters highly unstable. Prior art therefore relies on a process of calibration. For example, calibration means that of the five parameters needed to describe a physical system, four are determined independent of an assay measurement. The old assay process then proceeds by assuming the four parameters apply and are considered with a measurement of the fifth parameter, to be extracted from the assay measurement.

In the present invention, the assay solution comes from the solution of a coupled set of equations where all five parameters are used to solve for a physical parameter of interest, such as multiplication. The present invention benefits from a complete understanding of an arbitrary chain and variously allows the extraction all five parameters, or four parameters given only one, or three parameters given only two, etc.

In the present invention neutrons are measured in a neutron detector and five parameters are determine (mass, multiplication, alpha ratio, efficiency, and time constant) that describe the object that is being assayed. The present invention makes an assay for the purpose of determining these five parameters, given that one does not know these five parameters.

A neutron is created by a physical process, either fission or an inducing nuclear reaction. The created neutron or neutrons then interact with the environment. If the environment contains more nuclear material (i.e., uranium), the first neutrons may create more neutrons by causing more fission or other nuclear reactions. The first and second and subsequent neutrons are the chain. A chain may start with an alpha particle creating a single neutron that subsequently creates hundreds of fissions. Another chain may start with a spontaneous fission creating three neutrons that go on to create hundreds of fissions. These chains evolve over time and some of the neutrons are absorbed or lost. Finally, some members of the chain are captured in a detector. The final captured neutrons may be counted as a simple sum or observed as a time dependent rate. What may start out as a chain of 1000 neutrons may result in a count of two neutrons during some snippet of time, in a detector. The specific numerical process of relating the relevant physical parameters (mass, multiplication, alpha ratio, efficiency, and time constant) to an observed quantity (how many 2's) is based on approximations in the prior art. Describing these chains, with all the numerical detail requires a way to relate the five physical parameters to how the chains are created.

The present invention provides a method of absolute nuclear material assay of an unknown source comprising counted neutrons from the unknown source and uses a model (theory) to optimally fit the measured count distribution. The present invention begins by analytically solving for and efficiently computing the entire fission chain probability distribution for any given set of physical parameters (mass, multiplication, alpha ratio, efficiency, and time constant). This fission chain distribution is then used to simulate a data stream from which time dependent count distributions are constructed. The model randomly initiates fission chains at a rate dependent on the measured source strength and samples from the analytical fission chain probability distributions to artificially create data with statistical fluctuations with finite time counting. This approach allows the most direct modeling of the data as it is actually taken. It also allows complete control in modeling issues related to finite sampling, truncation errors from inherently truncated data, and dead time effects in the detector.

Previous art could only compute the first few moments of the full idealized fission chain distribution and relate these to moments of measured data. The previous art is fundamentally flawed in modeling finite sample truncated data with idealized infinite population moments. This flaw manifests itself in an erratic and unstable reconstruction of the unknown physical parameters. The approach of the present invention, based on analytical fission chain probability distribution, is able to robustly and stably reconstruct physical parameters.

A far more reaching significance of the present invention is that it provides a complete theoretical framework for modeling the entire neutron count distribution, not just its first few moments. Any measured count distribution and its model made with the five, or even more parameters, may be quantitatively compared for the purpose of optimally reverse engineering the 5 or more parameters that describe the unknown. Previous art based on the first few moments can only get at some small subset of the information contained in the data, and even then is flawed by issues of finite sample size and truncation errors. (Other parameters include, but are not limited to background contributions, external sources adding counts, (n,2n) neutron sources . . . )

The present invention provides a method of absolute nuclear material assay of an unknown source comprising counting neutrons from the unknown source and providing an absolute nuclear material assay utilizing a sampling method to distribute theoretical count distributions over time. The method utilizing a random sampling of a count distribution to generate a continuous time-evolving sequence of event-counts by spreading the count distribution in time. The present invention also provides an apparatus for absolute nuclear material assay comprising a multigate neutron multiplicity counter, a processor that solves three moment equations, a processor that provides fit to actual time dependence of the moments to get proper asymptotic moments, a processor that uses the estimated parameters to compute full count distribution, a processor that compares truncated data moments with untruncated and truncated theoretical moments, and a processor that provides adjustments to reduce bias.

The present invention has use in providing an assay of nuclear material. The present invention also has uses in providing the amount of moderator and in providing a neutron lifetime. The present invention can be used to providing an operator a simple system for obtaining the mass, multiplication, detector efficiency, and the alpha-decay-created neutron rate.

The invention is susceptible to modifications and alternative forms. Specific embodiments are shown by way of example. It is to be understood that the invention is not limited to the particular forms disclosed. The invention covers all modifications, equivalents, and alternatives falling within the spirit and scope of the invention as defined by the claims.

BRIEF DESCRIPTION OF THE DRAWINGS

The accompanying drawings, which are incorporated into and constitute a part of the specification, illustrate specific embodiments of the invention and, together with the general description of the invention given above, and the detailed description of the specific embodiments, serve to explain the principles of the invention.

DETAILED DESCRIPTION OF THE INVENTION

Figure 1:
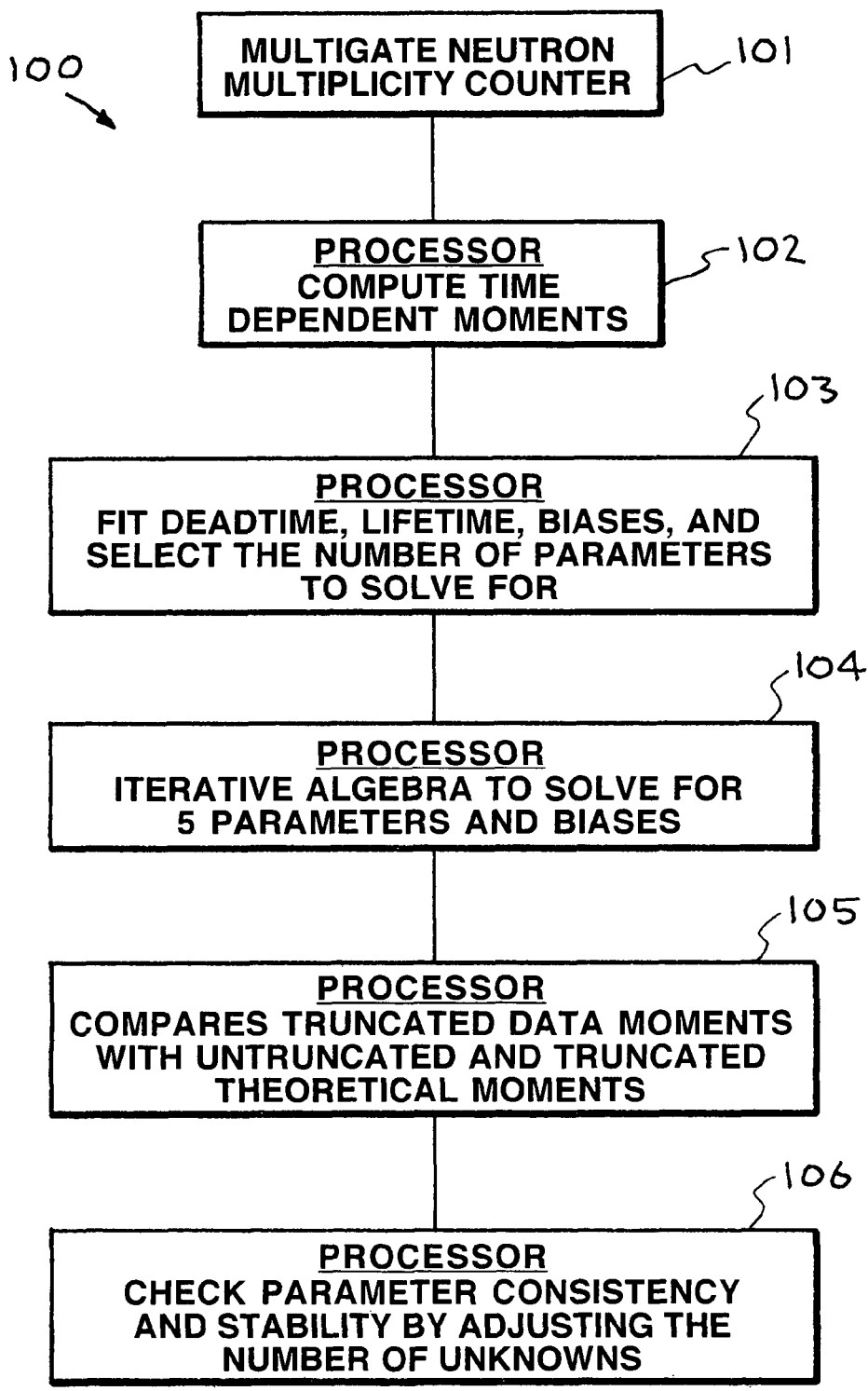
FIG. 1 illustrates one embodiment of a system incorporating the present invention.

Referring to the drawings, to the following detailed description, and to incorporated materials, detailed information about the invention is provided including the description of specific embodiments. The detailed description serves to explain the principles of the invention. The invention is susceptible to modifications and alternative forms. The invention is not limited to the particular forms disclosed. The invention covers all modifications, equivalents, and alternatives falling within the spirit and scope of the invention as defined by the claims.

Fission is defined as the emission of multiple neutrons after an unstable nucleus disintegrates. For example, Pu240 decays at a rate of about 400 fissions per second per gram of Pu240 atoms. When the fission occurs, multiple neutrons are emitted simultaneously, with the number ranging from zero to eight neutrons. The present invention provides a system that utilizes a set of parameters that describe an unknown mass of fissile material. This simultaneous neutron emission characteristic is unique to fission. The present invention provides a system that utilizes a multiplicity counter and a neutron detector that is set up to see time grouped neutrons. The present invention has use in providing an operator a simple system for obtaining the mass, multiplication, detector efficiency, and the alpha-decay-created neutron rate.

The characteristic of fission is that neutrons emit in groups. Random sources of neutrons are emitted with no regard for grouping, however, since the appearance of these neutrons at the detector are randomly spread in time, some may accidentally appear in close temporal proximity. An example is a neutron detector that counts neutrons for short periods of time, say ½ milli-second. This example time corresponds to a typical neutron diffusion time in a typical detector, the choice of which depends on the detector design and is not the subject here. If the ½ msec. period is counted once, the count may be three counts, or some other integer number, including zero. It is desirable to select an appropriate observation time, two to three times the typical neutron diffusion time, and then repeat the sampling of counts period many times to produce a histogram of counts described as the number of occurrences of each multiplet group (i.e., number of times 0, 1, 2, 3 . . . were observed, in sum, over say 10,000 repeated detection periods).

Fission is unique in that it creates real correlations, while non-fission neutron sources create accidental correlations. The present invention provides a system that utilizes new developments in how fission neutron chains are modeled to simplify and remove problems related to the assay of unknown packages of fissioning material. In general, the present invention provides a system that describes the evolution of fission chains with enough detail that universal procedures can be defined for absolute assay. The absolute assay does not need pre-defined facts or assumptions about the neutron detector efficiency (e), neutron lifetime (L), instrumentation dead-time losses (D), the terrestrial background (B), or the fraction of alpha-decay-induced neutrons (A) while endeavoring to obtain neutron multiplication (M) and mass of fissioning material (m).

Counting neutrons by looking for time-correlated groupings is called multiplicity counting. The groupings arise from the fission process where a portion of a fission chain is detected. The analysis of this type of data assists in deriving mass, multiplication, detector efficiency, and alpha ratio (mMeA). Other factors in the analysis include neutron lifetime (L), measurement gate width (T), the maximum size of neutron multiplets observed (n), the background correlation and count rate (B), and the generalized Poisson exponent $\Lambda$ ($\Lambda$). Traditionally, the count rate (singles) and the number of doubles are used to solve for up to two of the parameters, unfortunately with a significant dependence on quantitative knowledge of the other parameters. Measurement of the number of singles and doubles is limited additionally because of the necessity of incomplete sampling of the fission chains (since no one can count for an infinite time). Prior approaches assume a complete sampling of the fission chain. The present invention provides a system that utilizes a process where the partial and full fission chain details are calculated exactly and are used to correctly interpret the measurements. The present invention provides a system that utilizes allows solving for all of the unknown parameters listed above.

The premise for (definition) multiplication is that all neutrons in the fission chains are accounted for in the definition of nubar and multiplication (M). Nubar of the fission chain (N) and M must relate exactly (probability of fission=p) $M=1/(1-pN)$. The first moment of the induced fission chain, started from one neutron, is $(1-p)M$ and is what is intended to be measured. In practice the first moment is not actually measured because the populations of neutrons are always sampled incompletely. M is the multiplication defined for the full population. Measurement gives an incomplete sampling of the population and is always biased (incorrect) because of the finite sampling time. When the measured samples are biased, they no longer relate properly to the M derivation, therefore M is usually derived only approximately. The incomplete sampling problem applies to higher moments of the fission chain. These errors propagate to the other derived unknowns, regardless of how many moments are used in an analysis. Other errors arise from mistakes in understanding the matrix of unknown source containers (e.g., errors in L, A, e, and B).

The present invention provides a system that utilizes measurements made with a multi-gate neutron multiplicity counter. A fit to the actual time dependence of the moments is used to get the proper asymptotic moments and dead-time losses inherent in the data. Since H-$C^2$ inversion leads to estimates that are biased (wrong) because of the finite sampling problem and dead-time, there are two paths to solve for the rest of the parameters. One is to use the Prasad theory to compute libraries of count distributions that may be used as a lookup table and the other is to use the H-C style estimated parameters to compute the full count distribution that would have been measured if there was no finite sampling error. The present invention provides a system that compares the truncated data moments (measurement) with untruncated and truncated theoretical moments.

The present invention provides a system that utilizes extending the moments approach to more unknowns. Also, using moments is the same as using only part of the measured data, in contrast to actually fitting the measured count distribution to a library of count distributions (theory). The present invention provides a system that utilizes furthering the field by fitting the measurement to theoretically calculated count distributions to find the optimal set of parameters that would explain the count distribution. Fitting the full count distribution is a better approach because it uses all the information in the count distribution. The present invention provides a fitting approach that can extract all unknowns, in contrast to the prior situation of deriving at most three unknowns from three moments. The present invention provides a system that extends the H-C approach by adding a new method for dead-time correction most noteworthy for high multiplication, allows for truncation corrections, and allows direct comparison of data to parameter-based (mMea) count distributions that are generated as a proof test.

The present invention provides a system that utilizes several new steps, not all required depending on analysis objectives or measurement uncertainties. One is to create a fitting algorithm that preferentially weights the longer T gates in a fitting analysis so the short mode effects minimally alter the resulting assmyptote. This is called a "T-cut" approach that prefers to extract the fundamental mode. Another method is to observe dead-time effects as a function of T, by simulation with Applicants new count distribution calculation method. This results in multi-mode time dependences that may be specified to the data fitting process, so that D may be extracted. With specific time-dependence specification and understanding, the fitting routine is stable as the only free parameter is D. Another method is to specify the time dependence in terms of the fission chain topology. This results in two modes for the second moment time dependence, and three modes for the third moment time dependence. By specifying these constrained sets of time dependences, the fitting routine will be stable as the only free parameter is the assmyptote and $L_{short}$ and $L_{long}$. The present invention provides a system that utilizes computing the exact fission chain time evolution and count distribution as a function of M, m, eA, L, T, A, D, and B so that Applicants can simulate measurements.

Regarding dead-time (D), a precursor to using count distributions for assay requires a method to add the dead-time. The present invention provides a system that utilizes distributed theoretical count distributions over time (i.e., time-tagging the count events as they would have been seen during a measurement). This is different from using a monte-carlo transport technique because such a technique can not sample rare events thoroughly enough. The Prasad count distribution generation technique completely fills in all rare events exactly so it can be sampled with uniform weight to form an accurate time-tagged stream of synthetic data. The present invention provides a system that utilizes random sampling of a count distribution to generate a continuous time-evolving sequence of event-counts spreads the count distribution in time, as it would have been seen during the measurement. This is done by randomly initiating fission chains at a rate dependent on the source strength and sampling from Applicants analytical theory of fission chain probability distributions to artificially create a stream of realistic data. The final step is to alter the time-tagged data with "coincidence-sum limits" to create dead time in time-tagged data or summed-count distributions. "Coincidence-sum limits" are the removal of selected time-tagged counts based on their being located within a D seconds to another count. Here D would be called the dead-time.

The present invention provides a system that utilizes dealing with dead time when using H-C style moments based analysis. Similar to the process of generating a count distribution, the impact of dead-time is a non-linear process at the core of the count distribution generating function. Having identified the impact of dead time on count distributions, the present invention provides a system that parameterized these effects in the form of corrections to the moments.

First moment: $D_{cr} = T_{cr} \exp(-DT_{cr} - DLT_{r2f})$.

Second moment: $D_{r2f} = T_{r2f} \exp(-D[3T_{cr} - LT_{r2f} + \{2LT_{r3f}/T_{r2f}\}])$.

Third moment: $D_{r3f} = T_{r3f} \exp[-D[5T_{cr} - LT_{r2f} + \{(2T_{cr}T_{r2f}^2 + 3LT_{r4f})/T_{r3f}\}]]$ Term Definition:

$D_{cr}$, $D_{r2f}$, and $D_{r3f}$ are the dead-time reduced count rate, second moment and third moments.

$T_{cr}$, $T_{r2f}$, and $T_{r3f}$ are the true, no-dead-time count rate, second moment, and third moments.

The process to correct moment-based dead time is to use dead-time afflicted count distributions (Applicants theory or measurements) to observe (fit) the perturbation in time dependence. Time dependences created by this method may be used to fit observed measured data to infer the amount of dead-time D. Then one may sequentially compute corrections to the moments starting with the count rate: $D_{cr} = T_{cr} \exp(-DT_{cr} - DLT_{r2f})$. Note the first iteration uses the observed data r2f. Then use $D_{r2f} = T_{r2f} \exp(-D[3T_{cr} - LT_{r2f} + \{2LT_{r3f}/T_{r2f}\}])$. This next step uses the observed data r3f. Next, compute $D_{r3f} = T_{r3f} \exp[-D[5T_{cr} - LT_{r2f} + \{(2T_{cr}T_{r2f}^2 + 3LT_{r4f})/T_{r3f}\}]]$.

Note this last step uses r4f which Applicants set equal to zero the first time through this process. Then one solves the three equations for the three unknowns. Now Applicants have the first estimate of Tcr, Tr2f, and Tr3f. Now Applicants feed them to the H-C algebra to get an estimate of mMeA. Next Applicants compute what Tr4f would be if the H-C algebra were correct. Then Applicants repeat the process started with the count rate data, now using the estimated Tr4f. Iteration continues until Tcr, Tr2f, Tr3f don't change from one iteration to the next. The final feed of Tcr, Tr2f, Tr3f into the H-C theory results in the true mMeA.

The present invention provides a system that includes the effects of background. Background comes from cosmic ray interactions in the detector, surrounding structures, the unknowns' non-fissile mass, or fissioning uranium in terrestrial material. The basic idea is to use the generating function to reverse engineer the Λ's in background. The present invention provides a system that measures background with one of Applicants counters, in the presence of large masses of iron, lead, and polyethylene. Specifically, the process is to compute the natural log of the background count distribution generating function and solve for the Λ's. The present invention provides a system that utilizes the background as a free parameter in generating data to develop specific understanding, or to partition an unknown measurement into the fraction of background present at measurement time. This approach is technically superior since fission chains are created from the non-linear process and not simply additive environmental fissioning mass.

The present invention provides a system that utilizes hundreds of time dependent gates T, is that a table of T versus L may be measured and used as a lookup to characterize the general state of moderation in an unknown object. The general method allows one to estimate the mass of hydrogenous moderator mixed with fissioning material. This knowledge is useful for waste barrels where hydrocarbons in the presence of alpha-emitting fissile material tend to liberate hazardous gases.

The present invention provides a system that utilizes data visualization techniques that give insight into the physics and the impact of statistical fluctuations on derived quantities.

The present invention comprises the steps of counting neutrons from the unknown source and providing an absolute nuclear material assay. In one embodiment the step of providing an absolute nuclear material assay comprises utilizing a sampling method to distribute theoretical count distributions over time. In one embodiment the step of providing an absolute nuclear material assay comprises utilizing a random sampling of a count distribution to generate a continuous time-evolving sequence of event-counts by spreading the count distribution in time. In one embodiment the step of providing an absolute nuclear material assay comprises altering time tagged data with "coincidence-sum limits" to create dead-time in time-tagged data or summed-count distributions. In one embodiment the step of providing an absolute nuclear material assay comprises observing fine resolution of T axis data to obtain modal structure. In one embodiment the step of providing an absolute nuclear material assay comprises H-C Point-model extension by using constrained sums of T dependence, to select best L to fit the data which includes T-cut approach to get long-mode asymptotes, multiple mode sums to get asymptotes, and single mode fits to see deviations from single mode behavior. In one embodiment the step of providing an absolute nuclear material assay comprises H-C Point-model extension by using constrained sums of T dependence, to select best L to fit the data which includes T-cut approach to get long-mode asymptotes, multiple mode sums to get asymptotes, and single mode fits to see deviations from single mode behavior and subsequently, use the best fit parameters from the model for analysis. In one embodiment the step of providing an absolute nuclear material assay comprises dead-time correction based on T dependence perturbations/shifts. In one embodiment the step of providing an absolute nuclear material assay comprises using L to estimate moderator mass around the fissioning material. In one embodiment the step of providing an absolute nuclear material assay comprises precomputing lookup tables of real-time computed count distributions for comparison to measured data.

Referring to FIG. 1, one embodiment of a system of the present invention is illustrated. This embodiment of the system is designated generally by the reference numeral 100. The system 100 comprises a number of interconnected structural components. The structural components include a multigate neutron multiplicity counter 101, a processor that computes the time dependent moments 102, a processor that provides fits to deadtime, lifetime, biases, and allows the selection of the number of unknown parameters 103, a processor that solves for the unknown parameters 104, a processor that compares truncated data moments with untruncated and truncated theoretical moments 105, and a processor that checks for consistency and stability of solutions 106. The system 100 can be used to provide an assay of nuclear material and/or to provide the amount of moderator, neutron time constant, or other biases. Note that process 104 is described in tables 2 and 3, and process 105 depends on the process in table 1.

Alternatively, count distributions may be generated from first principles. Table 3 includes a discussion and process ramp-up about BIGFIT.

The present invention provides a system that relates, in detail, a correlated or uncorrelated chain of neutrons with what appears in an instrument (i.e., relates physical parameter to a measured quantity). How the chain of neutrons is used was traditionally related in a process that connects count sums to physical parameters of interest, such as multiplication. The limitations of prior art start with and are rooted in approximations in the detailed description of the neutron chain. These approximations, in the details of exactly how a chain is described and evolves in time, conspire to make the process of relating chains to physical parameters highly unstable. Prior art therefore relies on a process of calibration. For example, calibration means that of the five parameters needed to describe a physical system, four are determined independent of an assay measurement. The old assay process then proceeds by assuming the four parameters apply and are considered with a measurement of the fifth parameter, to be extracted from the assay measurement.

In the present invention, the assay solution comes from the solution of a coupled set of equations where all five parameters are used to solve for a physical parameter of interest, such as multiplication. The present invention benefits from a complete understanding of an arbitrary chain and variously allows the extraction of all five parameters, or four parameters given only one, or three parameters given only two, etc.

In the present invention neutrons are measured in a neutron detector and five parameters determine (mass, multiplication, alpha ratio, efficiency, and time constant) that describe the object that is being assayed. The present invention makes an assay for the purpose of determining these five parameters, given that one does not know these five parameters.

A neutron is created by a physical process, either fission or an inducing nuclear reaction. The created neutron or neutrons then interact with the environment. If the environment contains more nuclear material (i.e., uranium), the first neutrons may create more neutrons by causing more fission or other nuclear reactions. The first and second and subsequent neutrons are the chain. A chain may start with an alpha particle creating a single neutron that subsequently creates hundreds of fissions. Another chain may start with a spontaneous fission creating three neutrons that go on to create hundreds of fissions. These chains evolve over time and some of the neutrons are absorbed or lost. Finally, some members of the chain are captured in a detector. The final captured neutrons may be counted as a simple sum or observed as a time dependent rate. What may start out as a chain of 1000 neutrons may result in a count of two neutrons during some snippet of time, in a detector. The specific numerical process of relating the relevant physical parameters (mass, multiplication, alpha ratio, efficiency, and time constant) to an observed quantity (how many 2's) is based on approximations in the prior art.

Describing these chains, with all the numerical detail requires a way to relate the five physical parameters to how the chains are created. This procedure is summarized in Table 1 below.

TABLE 1

$$x = \int_0^t e^{-\lambda(t'-t_f)} \lambda\, dt' = e^{\lambda t_f}(1-e^{-\lambda t}),$$

$$y = \int_{t_f}^t e^{-\lambda(t'-t_f)} \lambda\, dt' = (1-e^{-\lambda(t-t_f)}),$$

$\lambda$ is lifetime.
t is time
$\epsilon$ is efficiency $$\bigwedge\nolimits_f = \left\{ \int_{-\infty}^0 \left[\sum_{v=f}^\infty P_v \binom{v}{j}(\epsilon x)^j (1-\epsilon x)^{v-j}\right] F_s dt_f + \int_0^t \left[\sum_{v=j}^\infty P_v \binom{v}{j}(\epsilon y)^j (1-\epsilon y)^{v-j}\right] F_s dt_f \right\}.$$

$F_s$ is p/s (mass)
$P_v = f(M, v(snm))$
A comes from a special case of a single neutron multiplying For example, the number of fives is:

$$b_5 = \left( \bigwedge\nolimits_5 + \bigwedge\nolimits_4 \bigwedge\nolimits_1 + \bigwedge\nolimits_3 \bigwedge\nolimits_2 + \bigwedge\nolimits_3 \frac{\Lambda_1^2}{2!} + \frac{\Lambda_2^2}{2!}\bigwedge\nolimits_1 + \bigwedge\nolimits_2 \frac{\Lambda_1^3}{3!} + \frac{\Lambda_1^5}{5!} \right)$$

$\exp[-(\Lambda_1 + \Lambda_2 + \ldots)]$.

Bn is the multiplet count in the measurement and is directly related to the five parameters with this calculation process. A multi-gate counter measures Bn as a function of lifetime and neutron number.

Since degenerate use of the procedure of the present invention is possible, Applicants made a NMAC procedure. It is similar to the hage-Cifferelli moments approach, but the NMAC procedure extends that procedure by allowing solutions that may be truncated as all measurements are, allows detailed time dependent analysis to better understand time truncated measurements, allows for the inclusion of gamma-rays in the assay process, and allows for dead time correction for the second and higher moments. The NMAC procedure is summarized in Table 2 below.

TABLE 2

NMAC solves algebra solutions based on the first 3 moments.
We always fit λ to determine neutron lifetime and therefore correct for asymptotic saturation.
This leaves four unknowns to determine: m, M, A, ϵ.
Case examples:

Given one unknown and R1, R2, and R3, we solve for the remaining unknowns (e.g. Given A, we solve for m, M, and ϵ).
Given two unknowns and R1 and R2, we solve for the remaining two unknowns (e.g. Given A and ϵ, we solve for m and M)

A comparison of the NMAC procedure and the BigFit procedure is summarized in Table 3 below.

TABLE 3

Neutron Multiplicity Analysis Code (NMAC)

Mass, Multiplication, Alpha, efficiency, Lambda are unknown.
R2 = mass [$\epsilon^2 M^2 q^2 (D_{2s} + M - 1(1+A)D_2)$] F(λt) and describes one of the moments of the count distribution, which is only a piece of the count distribution information.
NMAC solves algebra solutions based on the first 3 moments.
We cannot know efficiency if we don't know the geometry
We cannot solve for five unknowns with three equations (e.g. y1, y2, y3)
Higher moments algebra (y4, y5) depends too much on the tail, i.e. noisy.
Algebra involves ratios of moments, where uncertainties in the moments cause large solution errors.
BigFit Alternatively, count distributions may be generated from first principles. Count distributions are the complete realization of the fission chain, related to all of the measured physical parameters and therefore provide all the available information and therefore the most definitive connection to the assay quantities that we want.
As a process, template fitting searches for a match between an unknown measurement and a library of variations. It appears that a library of ~4,000 variations and about $10^6$ counts is sufficient to provide a good match to the assay of the unknown.

Figure 2:
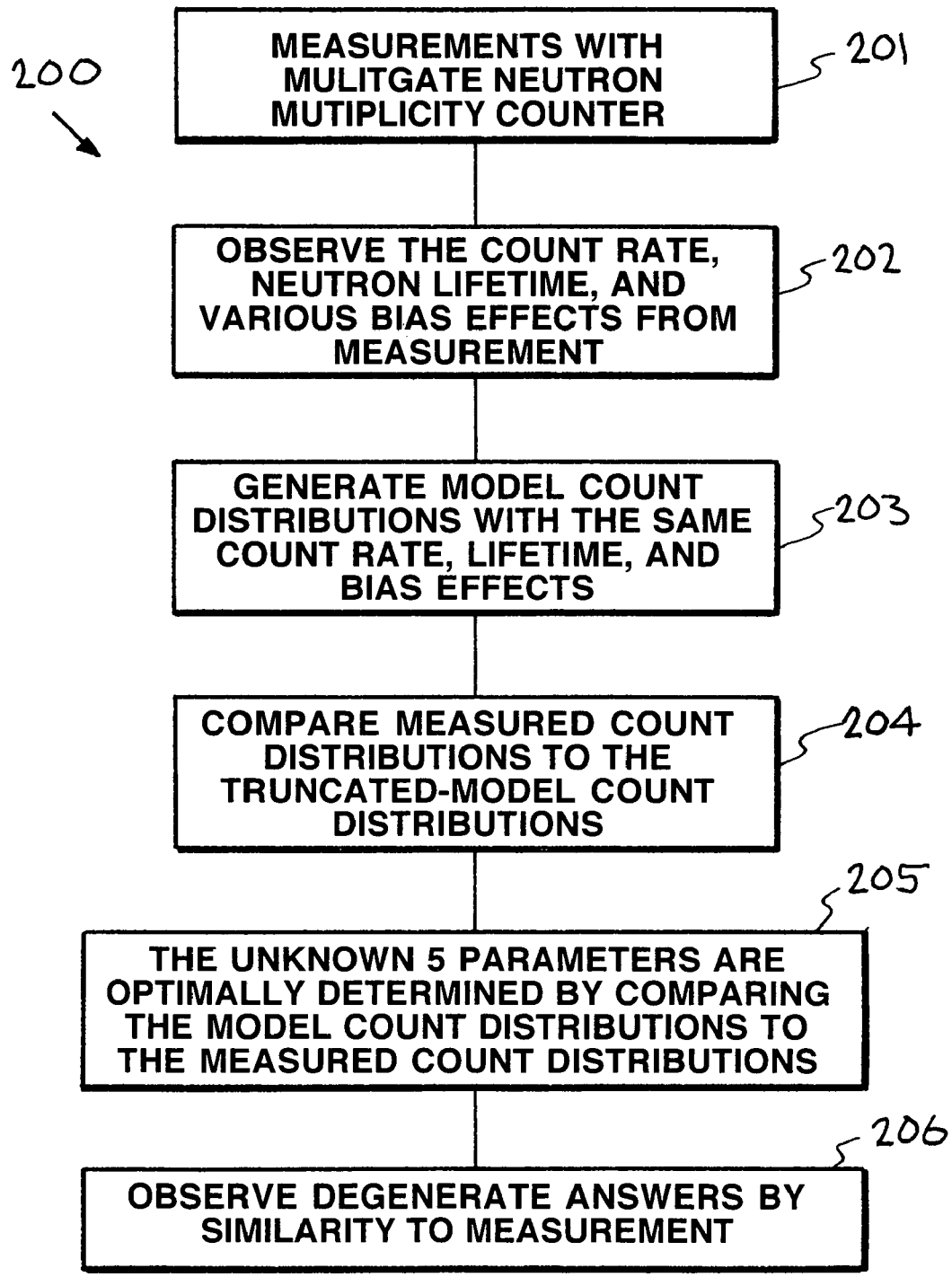
FIG. 2 illustrates another embodiment of a system incorporating the present invention.

Referring to FIG. 2, an embodiment of a system utilizing the present invention is illustrated. This embodiment is designated generally by the reference numeral 200. The system 200 provides a system for absolute nuclear material assay of an unknown source. The system 200 comprises the steps of counting neutrons from the unknown source and providing an absolute nuclear material assay. In one embodiment, the step of providing an absolute nuclear material assay comprises utilizing a sampling method to distribute theoretical count distributions over time. In another embodiment, the step of providing an absolute nuclear material assay comprises utilizing a random sampling of a count distribution to generate a continuous time-evolving sequence of event-counts by spreading the count distribution in time. In another embodiment, the step of providing an absolute nuclear material assay comprises altering time tagged data with "coincidence-sum limits" to create dead-time in time-tagged data or summed-count distributions. In another embodiment, the step of providing an absolute nuclear material assay comprises observing fine resolution of T axis data to obtain modal structure. In another embodiment, the step of providing an absolute nuclear material assay comprises H-C Point-model extension by using constrained sums of T dependence, to select best L to fit the data which includes T-cut approach to get long-mode asymptotes, multiple mode sums to get asymptotes, and single mode fits to see deviations from single mode behavior. In another embodiment, the step of providing an absolute nuclear material assay comprises H-C Point-model extension by using constrained sums of T dependence, to select best L to fit the data which includes T-cut approach to get long-mode asymptotes, multiple mode sums to get asymptotes, and single mode fits to see deviations from single mode behavior and subsequently, use the best fit parameters from the model for analysis. In another embodiment, the step of providing an absolute nuclear material assay comprises dead-time correction based on T dependence perturbations/shifts. In another embodiment, the step of providing an absolute nuclear material assay comprises using L to estimate moderator mass around the fissioning material. In another embodiment, the step of providing an absolute nuclear material assay comprises precomputing lookup tables of real-time computed count distributions for comparison to measured data.

Sources of fission neutrons can be statistically distinguished from random neutron sources. A random source produces a Poisson distribution, $$b_n = \frac{C^n}{n!} e^{-C} \quad \text{Equation (1)}$$

for the probability to detect a particular number, n, during a counting window, where C is the average number of counts during that counting time. A fission source produces a distribution with a larger width. Since fission chains produce multiple neutrons in bursts, the larger width, or larger fluctuation, is related to the probability to detect more than one neutron from the same fission chain.

The form of the counting distribution for a fission source is a generalized Poisson distribution. Unlike the Poisson distribution that depends on only a single time dependent parameter, C=R t, where R is the count rate, the generalized Poisson distribution depends on many, in principle even an infinite number, of time dependent parameters, $A_k(t)$, k=1, 2, 3, . . . . If $b_n(t)$ is the probability to get n neuron counts in a time gate of length t, then, $$b_n = b_0 \sum_{i_1+2i_2+3i_3+\ldots+ni_n=n} \frac{\Lambda_1^{i_1} \Lambda_2^{i_2} \ldots \Lambda_n^{i_n}}{i_1! \, i_2! \ldots i_n!} \quad \text{Equation (2)}$$

where $i_k$ is the number of independent chains contributing k counts (for k=n, $i_n$=0 or 1, while for k=1, $i_1$=0, 1, 2, . . . , n), and $$b_0 = \exp[-(\Lambda_1 + \Lambda_2 + \ldots + \Lambda_n + \ldots)]. \quad \text{Equation (3)}$$

For example, the probability to get 5 counts is $$b_5 = \left(\Lambda_5 + \Lambda_4\Lambda_1 + \Lambda_3\Lambda_2 + \Lambda_3 \frac{\Lambda_1^2}{2!} + \frac{\Lambda_2^2}{2!}\Lambda_1 + \Lambda_2 \frac{\Lambda_1^3}{3!} + \frac{\Lambda_1^5}{5!}\right) \quad \text{Equation (4)}$$
$$\exp[-(\Lambda_1 + \Lambda_2 + \ldots)].$$

If all the $L_k$ but $\Lambda_1$ are zero, then $b5 \to \Lambda_1^5 e^{-\Lambda_1}/5!$, a Poisson distribution. The term $\Lambda_1^5 e^{-(\Lambda_1+\Lambda_2+\cdots)}/5!$ represents the probability that each of the 5 counts was due to an independent random source, where only a single neutron is counted from each independent chain. The term $\Lambda_5 e^{-(\Lambda+\Lambda_2+\cdots)}_L$ is the probability that all 5 counts arise from a common source, a single chain. The term $\Lambda_2^2 \Lambda_1 e^{-(\Lambda_1+\Lambda_2+\cdots)}/2!$, for example, is the probability that the 5 counted neutrons arise from 3 independent random sources, two pairs of counts each have a different common ancestor, and an additional count arises from a third source. For a weak neutron source in a system of high multiplication, it is likely to get multiple counts from the same chain, but the chains are few and far between. For a strong source in a system of low multiplication, the probability of getting multiple counts from a single chain is small, while the probability of getting many counts, most from independent chains, is high. So clearly information about the source strength and multiplication are encoded in the counting distribution. Applicants would like to have a complete theory relating the material and detector properties to the time dependent counting distribution. This requires a more complete theory of fission chains. In this paper Applicants develop an analytic formula for the t→∞ fission chain, and, in the approximation that at most two neutrons are emitted in an induced fission, a closed form expression for the time evolving fission chain. These formulas apply in the point model approximation, in which spatial dependence and neutron spectrum are neglected.

Referring again to FIG. 2, the system 200, comprises step 201 measurements with multigate neutron multiplicity counter, step 202 solve three moment equations, step 203, use fit to actual time dependence of the moments to get proper asymptotic moments, step 204 use the estimated parameters to compute the full count distribution, step 205 compare truncated data moments with untruncated and truncated theoretical moments, and step 206 making adjustments to reduce bias.

Measurements are made with the multigate neutron multiplicity counter 101. Three moment equations are solved with the truncated asymptotes to estimate three of the unknowns (MmeA), given one parameter. A fit to the actual time dependence of the moments is used to get the proper asymptotic moments. Since the estimates are biased (wrong) because of the finite sampling problem, Applicants use the estimated parameters to compute the full count distribution that would have been measured if there was no finite sampling error. Then Applicants compare the truncated data moments (measurement) with untruncated and truncated theoretical moments. Adjustments to reduce bias in the moments or count distributions are then possible via a data entry window.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims.

The invention claimed is:

1. An apparatus that provides an absolute nuclear material assay of an unknown source that emits neutrons, comprising:

a multigate neutron multiplicity counter detecting neutrons emitted from the source and grouped with respect to time, and collecting a number of neutrons within a defined time window to derive neutron multiplet count data, the multigate counter further measuring the multiplet count in a measurement as a function of lifetime and neutron number;

a processor of a plurality of processors coupled to the multiplicity counter and executing code to iteratively solve a plurality of coupled algebraic equations for five unknown parameters of the source using the first three moments of a fission chain distribution, wherein the parameters comprise mass, multiplication, alpha ratio, detector efficiency, and time constant (lambda), and wherein the first three moments are corrected with respect to the impact of instrument dead time on the count distributions of the emitted neutrons;

another processor of the plurality of processors coupled to the multiplicity counter executing code that fits the time constant parameter to the actual time dependence of the moments to reduce the unknown parameters to four parameters of mass, multiplication, alpha ratio, and detector efficiency; and yet another processor of the plurality of processors coupled to the multiplicity counter that executes code that compares truncated data moments with untruncated and truncated theoretical moments to provide an estimation of a parameter of the four parameters and to allow for solution of the remaining three parameters using the first three moments.

2. The apparatus of claim 1 wherein the correction of the first three moments with respect to dead time is performed by time-tagging the neutron count events as seen during a measurement and creating a fitting algorithm that preferentially weights longer time gates so that short mode effects minimally alter a resulting asymptote of the count distribution.

3. The apparatus of claim 2 wherein the first moment is a dead-time reduced count rate correction, and a first iteration produces a first estimate of the true count rate and the second and third moments.

4. The apparatus of claim 3 wherein the first estimate of the true count rate and the second and third moments is used to create an estimate of the fourth moment that is used to refine the estimate of the true count rate and second and third moments in subsequent iterative steps until no change is found, at which time the four parameters are determined.

* * * * *